United States Patent [19]

Tamai et al.

[11] 3,984,475
[45] Oct. 5, 1976

[54] PROCESS FOR THE PRODUCTION OF SUBSTITUTED KETONES

[75] Inventors: Yoshin Tamai; Takashi Nishida; Fumio Mori, all of Kurashiki; Yoshiaki Omura, Okayama; Masahisa Tanomura, Kurashiki; Takeo Hosogai, Kiyone; Yoichi Ninagawa; Kazuo Itoi, both of Kurashiki, all of Japan

[73] Assignee: Kuraray Co., Ltd., Kurashiki, Japan

[22] Filed: May 29, 1975

[21] Appl. No.: 581,854

Related U.S. Application Data

[63] Continuation-in-part of Ser. No. 417,202, Nov. 19, 1973, abandoned.

[30] Foreign Application Priority Data

Nov. 17, 1972  Japan.............................. 47-115989
Aug. 9, 1973  Japan................................ 48-89862

[52] U.S. Cl......................... 260/586 R; 260/590 R; 260/593 R; 260/591; 260/592
[51] Int. Cl.²........................................ C07C 45/00
[58] Field of Search............ 260/586 R, 590 R, 591, 260/592, 593 R

[56] References Cited
UNITED STATES PATENTS 3,668,255  6/1972  Meuly et al..................... 260/593 R
3,701,814  10/1972  Shilling et al................... 260/593 R

FOREIGN PATENTS OR APPLICATIONS 1,227,144  4/1971  United Kingdom................... 260/47

OTHER PUBLICATIONS

House, Modern Synthetic Reactions, 2nd Edition, (1972), pp. 546–570.

Primary Examiner—James O. Thomas, Jr.
Assistant Examiner—James H. Reamer
Attorney, Agent, or Firm—Bacon & Thomas

[57] ABSTRACT

Process for producing substituted ketones from the reaction between organic halides and ketones having replaceable active hydrogen atoms on the carbon atom(s) alpha to the carbonyl group, in the presence of an alkali metal hydroxide unitilizing phosphonium salts as the catalyst, which salts have the following formula:

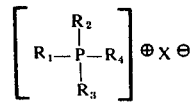

wherein said $R_1$, $R_2$, $R_3$ and $R_4$ are the same or different and are branched or straight chain alkyl of 1–30 carbon atoms, cycloalkyl of 6–10 carbon atoms, aryl of 6–10 carbon atoms aralkyl or alkaryl wherein the aryl and alkyl are as above defined and $X^-$ is an inorganic or organic anion.

26 Claims, 2 Drawing Figures

PROCESS FOR THE PRODUCTION OF SUBSTITUTED KETONES

This application is the continuation-in-part of the copending application Ser. No. 417,202, filed Nov. 19, 1973 now abandoned.

BACKGROUND OF THE INVENTION

1. Field of the Invention

The present invention relates to a catalytic process for producing substituted ketones by reacting an organic halide with a ketone in the presence of alkali metal hydroxide and a catalyst, the reaction proceeding via intermolecular liberation of hydrogen chloride.

More specifically, the instant invention relates to a process for preparing substituted ketones by reacting an organic halide with a ketone having one or more replaceable active hydrogen atoms on either or both of the carbon atoms alpha to the carbonyl group in the presence of an alkali metal hydroxide and certain catalytic phosphonium salts.

2. Description of the Prior Art

It is well-known in the prior art that substituted ketones may be prepared by reacting an organic halide with a ketone having replaceable active hydrogen atoms on the carbon atoms adjacent to the carbonyl group in the presence of alkali metal hydroxide and a catalyst, and the reaction mechanism is typically represented as follows:

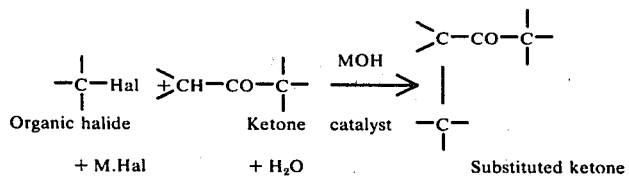

where M is an alkali metal.

For instance, according to the specification of U.S. Pat. No. 2,644,843, allyl methyl ketone reacts with alkyl halide in the presence of alkali-metal hydroxide.

Further, British Pat. No. 851,658 discloses that 6-methyl-4-heptene-2-one (hereinafter, referred to as "methyl heptenone") is produced by reacting 1-chloro-3-methyl-2-butene (hereinafter, abbreviated to "prenyl chloride") with acetone.

However, by the method described in the specification of the foregoing British Patent the yields obtained are 43% using potassium hydroxide, and as little as 20% with sodium hydroxide.

In the latest issue of the "Yuki Gosei-Kagaku (Journal of Organic Synthetic Chemistry, Japan)" 28, 54 (1970), experimental results obtained according to the method of the abovementioned British Patent indicate that the yields of substituted ketone were 35% using potassium hydroxide and less than 5% using sodium hydroxide, and that the yield was increasing by the addition of dimethyl formamide or dimethyl sulfoxide to the reaction system.

U.S. Pat. No. 3,668,225 also discloses the attainment of enhanced yields by the addition of amine compounds of various types.

According to the reaction set forth above, water is an inevitable reaction product and it is substantially impossible to carry out the reaction under absolutely anhydrous conditions.

It has heretofore been generally believed that the addition of considerable amounts of water to the reaction system at the beginning of the reaction should be avoided since presence of large amounts of water in the system considerably decreases the reaction yield. Conventionally, the amount of water in the system has been minimized by restricting the water content of the reactants and alkali metal hydroxide was added in solid form to the reaction system.

For example, it is stated in Japanese Pat. No. 40 (1965) 22,251, which corresponds to U.S. Pat. No. 3,668,255 that the dryness of the reactants is not critical when the reaction is effectuated in the presence of an aminecatalyst, and in most cases the reaction proceeds without impairment in the presence of not more than 2 moles of water per 1 mole of organic halide. However, it should be noted that in all the examples of said patents, the reactions were initiated under substantially anhydrous conditions.

According to the results of experiments performed by the present inventors, the reaction of prenyl chloride with acetone in the presence of alkali metal hydroxide was significantly inhibited by a very small amount of water present in the acetone, and further the yields of the reaction were definitely decreased by adding substances such as potassium iodide, sodium iodide, dimethyl sulfone, sulfolane, tri-n-butyl phosphine oxide, monomethyl amine, dimethyl amine, trimethyl amine, monoethyl amine, monocyclohexyl amine, ammonium chloride due to the presence of water in these reactants. Taking into account that a considerable amount of manufacturing cost is to be saved by omitting rigorous drying of the reacting materials, it is evident that this reduction in costs cannot be realized using conventional processing in which the permissible amount of water present in the reaction system must be limited to not more than 2 moles of water per 1 mole of organic halide.

SUMMARY OF THE INVENTION

The inventors of the present application have obviated the above-mentioned difficulties associated with prior art processes for preparing substituted ketone by providing a process wherein the water typically associated with the various reactants need not be removed prior to carrying out the reaction and, further, have discovered that the yield of substituted ketone may be increased in spite of the presence of water in the reaction system by the addition of certain catalytic phosphonium salts to the reaction system.

It has now been unexpectedly discovered by the present inventors that desired substituted ketones can be prepared without a reduction in yield in comparison with the yields obtained by conducting the reaction under anhydrous conditions and often with increased yields depending on the specific catalyst used, and further with excellent reproducibility of yield and reaction rate, by reacting the organic halide with the ketone in water in the presence of certain phosphonium salts as catalysts. According to the process of the present invention, the molar ratio of water to organic halide is not less than 2.5, the molar ratio of alkali metal hydroxide to water is not less than 0.3 and the molar ratio of alkali metal hydroxide to organic hakide is not less than 2.0.

In the present method it is permissible to add a sufficient amount of water to produce alkali metal hydroxide aqueous solutions, the reproducibility of the present reaction is very good with respect to rate of reaction as well as the reaction yield and the reaction proceeds at a controlled uniform rate.

Therefore, the present method has many industrial advantages in that reaction temperature can be readily regulated, the reaction process can be conducted with very minimal risk of harm to personnel, the reaction is carried out in simple laboratory apparatus, and the operation is conducted in a continuous process. Other advantages in addition to the above mentioned are as follows:

First, in the present method it is not necessary to use alkali metal hydroxide in powder or flake form, but rather alkali metal hydroxide pellets or aqueous solutions thereof may be utilized, both of which are readily available commercially at substantially lower cost than flake or powder forms.

It is especially advantageous to be able to introduce the alkali metal hydroxide as an aqueous solution, in that the feeding of the alkali metal hydroxide to the reaction system is facilitated, and further, the danger involved in handling solid alkali metal hydroxides in concentrated form is substantially avoided thereby improving the working conditions of the personnel.

Secondly, when alkali metal hydroxide is fed in the anhydrous state or close to the anhydrous state to the reaction system, alkali metal hydroxide in solid form occasionally adheres to the bottom of the reaction vessel, which prohibits the effective utilization of the alkali metal hydroxide in the reaction. To overcome this problem it is necessary to carefully attend to the operation of the reaction system, especially with respect to maintaining constant stirring in the reaction vessel. However, the problem is virtually nonexistent when alkali metal hydroxide is introduced as an aqueous solution.

Thirdly, the permissible amount of water contained in the reacting materials is considerably increased by the use of the present method, and recovery and reuse of unreacted ketone can be performed to reduce production costs.

Fourthly, in many cases, the present process reduces the required amount of ketone reactant for the production of substituted ketone in comparison with that of conventional methods.

Other objects and advantages of the present invention will be made apparent by reference to the drawings and description which follow.

DESCRIPTION OF THE PREFERRED EMBODIMENTS

Figure 1:
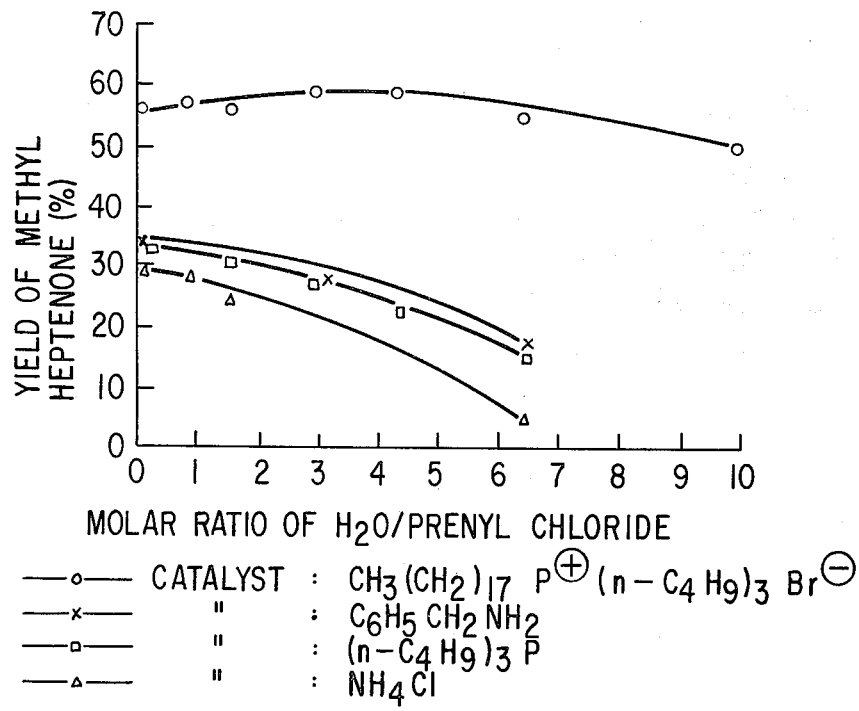
FIG. 1 depicts the effect the molar ratio of water to organic halide has on the yield of substituted ketone utilizing different catalysts.

Phosphonium salts suitable for use in the present invention are represented by the general formula

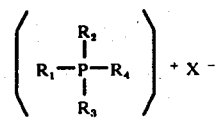

wherein $R_1$, $R_2$, $R_3$, $R_4$ are the same or different and selected from the group consisting of branched or straight chain alkyl of 1 to 30 carbon atoms, cycloalkyl of 6 to 10 carbon atoms, aryl of 6 to 10 carbon atoms and aralkyl or alkaryl wherein the aryl and alkyl moieties are as defined above and wherein $X^-$ is an inorganic or organic anion capable of dissociating from

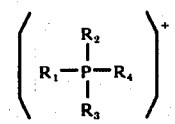

in an aqueous environment and capable of forming an alkali metal salt with an alkali metal hydroxide such as KOH or NaOH, for example, $Cl^-$, $Br^-$, $I^-$, $OH^-$, $NO_3^-$, $ClO_4^-$, $SO_4^{--}$, $PO_4^{---}$, $CH_3COO^-$,

$O_3SOCH_3^-$,

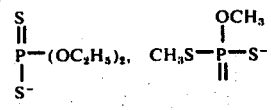

or

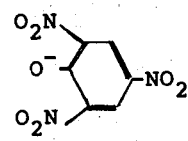

Since the anion composed of phosphonium salt does not take part in the formation of enolate and substituted ketone, various kinds of anions may be used as the anion of phosphonium salt.

Specific examples of compounds within the scope of the above generic formula include, bromide, iodide, hydroxide, nitrate, sulfate, acetate and the like described above of the following: tetramethyl phosphonium, tetraethyl phosphonium, methyl tripropyl phosphonium, diethyl dibutyl phosphonium, dibenzyl butyl methyl phosphonium, dicyclohexyl dimethyl phosphonium, dibenzyl dimethyl phosphonium, tetrabutyl phosphonium, dibenzyl ethyl methyl phosphonium, dibenzyl diethyl phosphonium benzyl tributyl phosphonium, tribenzyl methyl phosphonium, tribenzyl ethyl phosphonium, tri-n-butyl ethyl phosphonium, stearyl tributyl phosphonium, hexadecyl tributyl phosphonium, lauryl tributyl phosphonium, tricyclohexyl methyl phosphonium, tricyclohexyl ethyl phosphonium, tricyclohexyl n-butyl phosphonium, tricyclohexyl isobutyl phosphonium, tricyclohexyl n-propyl phosphonium, tricyclohexyl isopropyl phoshonium, tricyclohexyl amyl phosphonium, tricyclohexyl hexyl phosphonium, tricyclohexyl heptyl phosphonium, tricyclohexyl decyl phosphonium, tricyclohexyl lauryl phosphonium, tricyclohexyl tetradecyl phosphonium, tricyclohexyl hexadecyl phosphonium, tricyclohexyl stearyl phosphonium, tetracyclohexyl phosphonium, tricyclohexyl benzyl phosphonium, tri-4-methylcyclohexyl ethyl phosphonium and tri-4-methylcyclohexyl n-butyl phosphonium.

In practice the phosphonium salts of the present invention may be used alone or as a mixture of at least two types of them.

The concentration of the phosphonium salt added to the present reaction will vary depending upon the type of said salt, but generally it is in the range of about 0.05 to 20 mole per cent and preferably about 0.1 to 10 per cent based on the amount of organic halide present.

The organic halide and ketone reactants may be utilized in a molar ratio generally between 2:1 to 1:20, but preferably about 3 to 10 for the molar ratio of ketone to organic halide.

The catalyst of the present invention can be employed in anhydrous state to initiate the reaction, but the addition of water, in an amount in excess of about 2.5 moles and less than about 10 moles per 1 mole of organic halide is preferred in order to attain the reproducibility of the reaction and the other advantages mentioned above. The addition of water to the reaction system significantly contributes to the smooth operation of the reaction and to reducing the production costs.

In order to secure good yields of substituted ketone, it is recommended that the alkali metal hydroxide be used in an amount more than 1.1 mole per 1 mole of organic halide, when the reaction is initiated either under anhydrous conditions or in the presence of a small amount of water. For the case in which a relatively large amount of water is to be added, as described previously, the quantity of alkali metal hydroxide should be more than about 2 moles per 1 mole of organic halide and, further, an amount more than about 0.3 mole for each mole of water. Preferably, the amount of alkali metal hydroxide used is between about 2.5 to 4 moles per o mole of organic halide and between about 1.35 to 0.85 mole for each mole of water.

Generally speaking, there is no need to use alkali metal hydroxide in an amount in excess of 5 moles per mole of organic halide or more than 1 mole per 1 mole of water.

Satisfactory results may be obtained when less expensive sodium hydroxide is utilized as the alkali metal hydroxide.

Potassium hydroxide may also be employed either instead of or in the presence of sodium hydroxide. Alkali metal hydroxide is added to the reaction system in solid form with separately added water, but is most advantageously added as an aqueous solution of 45% to 65% by weight which facilitates the feed of the alkali metal hydroxide to the reaction system, reduces the possibility of injury to workers and generally increases the reaction yield and the rate of the reaction.

The reaction temperature ranges generally between 0°C. and 150°C., and preferably between 40°C. and 80°C. for optimum reaction rate and the reaction yield. The reaction can be performed under atmospheric pressure when the reaction mixture does not evidence a tendency to boil at the reaction temperature, or if desired, the reaction may be conducted under either increased or reduced pressure. The reaction can be conducted conveniently under refluxing conditions and atmospheric pressure at a temperature at which at least one component of the reaction mixture boils. When the starting materials employed are especially low boiling, the reaction may be carried out in a closed system at a reduced pressure.

The required time for completing the reaction varies according to the starting materials utilized, reaction temperature, and the extent of desired conversion, but generally it is desirable to continue the reaction until virtually all of the organic halide reactant has been consumed. Usually, the organic halide will be completely consumed in between 10 minutes and 30–40 hours.

In one embodiment of the present invention, conventional liquid-phase reaction procedures and-installation can be employed. In most cases a mixture of organic halide and ketone is first prepared. The removal of water from the mixture is not required since water present in the mixture does not adversely affect the reaction according to the present invention.

The the foregoing mixture, the hydroxide aqueous solution and then phosphonium salt are added or in vice versa order to effectuate the initiation of the reaction.

As far as the time required for supplying the reactant materials to the system is concerned, the feed may be accomplished over a period between 5 and 30 minutes and the order in which the reactants are added has little or no effect on the reaction rate or yield. Moreover, the alkali metal hydroxide and phosphonium catalyst may be added together.

As can be seen from the above description, by "initiation of reaction" it is meant that organic halide, ketone, alkali hydroxide, phosphonium salt and water (if the reaction is conducted in the anhydrous state, no water is added to the reaction system) are fed to the reaction system and the temperature raised to a certain pre-determined reaction temperature, and by "initiation of reaction" there is not meant any further strict definition.

The reaction should be allowed to continue until the quantity of organic halide fed is consumed almost completely.

After the reaction proceeds to completion in the reaction liquid, a precipitate of alkali halide is formed as a consequence of alkali hyroxide reacting with hydrogen halide produced by the reaction organic halide with ketone. Usually, water is added to the reaction liquid in order to dissolve said alkali halide and to decompose residual organic halide, and the resultant liquid is separated into two layers, organic and water. The organic compound containing layer is subjected to further separatory processes such as distillation to recover the products. Unreacted ketone which is recovered with the above procedure is cycled back to the system for reuse. In case the reaction liquid contains unreacted starting material of relatively low boiling point such as acetone, at an appropriate time ater completing the reaction and prior to separation of the liquid into organic compound and water layers, said unreacted material may be recovered by an evaporation procedure. Furthermore, the reaction liquid containing alkali metal hydroxide as a form of precipitate is subjected to filtration and the filtrate is treated to separate same into organic compound and water layers, ketone product being separated from the organic compound layer. The water layer, which is separated from the reaction liquid, is fed back to the reaction system for reuse and, if required, is subjected to concentration procedures and/or fresh alkali metal hydroxide is added to the water layer before reuse.

In a conventional process, in which anhydrous alkali metal hydroxide is employed to initiate the reaction, it is very difficult to recover alkali metal hydroxide from the reaction mixture for reuse, since unreacted alkali metal hydroxide is present in the mixture with alkali halide after the reaction.

The organic halide and ketone starting material utilized in the practice of the present invention are not required to be compounds with specially reactive chemical structure.

Non-limiting examples of organic halides which may be employed include alkyl halides, such as methyl chloride, methyl bromide, ethyl chloride, ethyl bromide, propyl chloride, propyl bromide and butyl chloride; alkenyl halide, such as 1-chloro-3-methyl-2-butene and citronenyl chloride; allyl halides, such as allyl chloride, allyl bromide, methallyl chloride, crotyl chloride, geranyl bromide, farnesyl chlorides and phutyl chloride; propargyl halide such as propargyl chloride and propargyl bromide; cycloalkyl halides such as cyclohexyl halide; benzyl halide and the like. The iodides as well as other anions of the foregoing are also suitable.

Suitable ketones for use in the method of the present invention are ketones having at least one active hydrogen on the carbon atom in the α-position to the carbonyl group.

Specific non-limiting examples of the ketone reactant include alkyl ketones, such as acetone, methyl ethyl ketone, diethyl ketone, methyl propyl ketone, methyl isobutyl ketone, ethyl butyl ketone, methyl amyl ketone, methyl isoamyl ketone and methyl hexyl ketone; alkenyl ketones or cycloalkenyl ketones, such as mesityl oxide, allyl acetone, methyl heptenone, and ionone; cycloalkyl ketones such as cyclopentanone, cyclohexanone and cycloheptanone; camphor and acetophenone; phenyl acetone and the like.

Substituted ketones prepared by reacting organic halide with ketone according to the process of the invention, include useful ketones, such as those utilized as intermediate compounds in various organic synthetic processes including the preparation of perfume. For instance, methyl heptenone which is obtained by reacting prenyl chloride with acetone is an important intermediate in the synthesis of vitamin E and perfume.

In order to further illustrate the present invention and the advantages thereof, the following specific examples are given, it being understood that the same are intended only as illustrative and in no way limitative.

EXAMPLE 1

Into a 200 ml. round-bottom flask equipped with a thermometer, a reflux condenser and a stirrer, were introduced 10.46 g of prenyl chloride, 51 ml. of acetone and powdered sodium hydroxide, the amount of which was adjusted to be equivalent to a molar ratio of between 0 to 10 corresponding to the molar ratio of water to each mole of prenyl chloride, or sodium hydroxide aqueous solution in which the quantity of sodium hydroxide is 3 times the molar quantity of prenyl chloride. 0.45 g of stearyl-tri-n-butyl phosphonium bromide was added to the mixed solution and then the resulting solution was stirred for 5 hours under reflux. After the reaction was completed, 40 ml. of water was added to the resulting solution to dissolve sodium chloride which has precipitated from the solution during the reaction. The production of methyl heptenone was determined using gas chromatography and the yield was calculated on a theoretical basis.

For reference samples, the same procedures as indicated above were repeated except tri-n-butyl phosphine, benzyl amine or ammonium chloride were utilized as the catalyst in place of stearyl-tri-n-butyl phosphonium bromide, each being present in a concentration of 1 mole per cent based on the amount of prenyl chloride.

The experimental results are shown in FIG. 1.

FIG. 1 shows the influence of water in the reaction system with the aforementioned catalysts of different types with respect to the yield of methyl heptenone. In the reaction, methyl heptenone was synthesized by reacting prenyl chloride with acetone in the presence of alkali metal hydroxide and a catalyst.

The ordinate of the graph in FIG. 1 is the yield of methyl heptenone (%) and the abscissa is the molar ratio of $H_2O$/prenyl chloride at the start of the reaction. Along the abscissa of FIG. 1, the integer 1 means that said reaction was initiated under the conditions of the reaction system at a molar ratio of 1 mol of water to the 1 mole of prenyl chloride, and the integer 10 means the reaction system at the start contained 10 moles of water and 1 mole of prenyl chloride.

As can be seen from the figure, when a phosphonium salt is used as the catalyst according to the present invention, methyl heptenone, the object of the synthesis, was obtained in high yield even in a reaction system wherein a large amount of water was already present at the beginning of the reaction, and the yield of methyl heptenone was not affected by the content of water in the system.

EXAMPLE 2

Into the same reaction vessel as used in Example 1, 10.45 g of prenyl chloride, 51 ml. of acetone, 24 g of sodium hydroxide (50% aqueous solution), 5 ml. of n-decane (used as an internal standard for gas chromatography) and 0.31 g of tri-n-butyl ethyl phosphonium bromide were introduced and the reaction was carried out under violent stirring for 4 hours.

As reference samples, the same procedure as indicated above was repeated except $(n-C_4H_9)_4NOH$ (10% aqueous solution) and 1 mole % of $(CH_3)_4 NCl$ per mole of prenyl chloride were used in place of tri-n-butyl ethyl phosphonium bromide.

The yield of methyl heptenone at various reaction times was determined for each of the three reaction systems. The experimental results are shown in FIG. 2.

Figure 2:
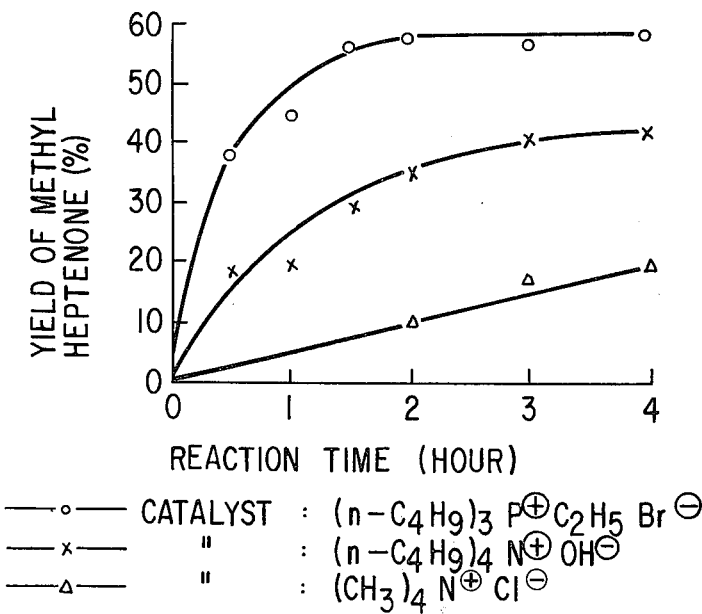
FIG. 2 shows the effect various catalytic compounds have on the yield of substituted ketone.

FIG. 2 shows the influence of various catalysts of different types on the yield of methyl heptenone. In the reaction, methyl heptenone was synthesized by reacting prenyl chloride with acetone in the presence of alkali metal hydroxide.

As can be seen in FIG. 2 the use of a phosphonium salt of the present invention considerably increases the yield of methyl heptenone.

EXAMPLES 3 to 8

Using the same reaction vessel as used in Example 1, 10.45 g of prenyl chloride, 51 ml. of acetone and 24 g of sodium hydroxide 50% aqueous solution were mixed and the various types of phosphonium salts indicated below were added at the concentration of 1 mole % based on the amount of prenyl chloride, and the reaction mixture was refluxed with stirring.

Upon completion of the reaction, the product was determined to be methyl heptenone by gas chromatography and the theoretical yields were calculated with the following results:

| Example | Catalyst Used | %* |
|---|---|---|
| 3 | $(n-C_4H_9)_3P^+CH_3B^-r$ | 52.3 |
| 4 | $(n-C_4H_9)_4P^+B^-r$ | 53.6 |
| 5 | $C_6H_{11}P^+(n-C_4H_9)\ Cl^-$ | 58.3 |
| 6 | $CH_3(CH_2)_{11}P^+(n-C_4H_9)_3Br^-$ | 58.2 |
| 7 | $CH_3(CH_2)_{15}P(n-C_4H_9)_3Br$ | 61.0 |
| 8 | $(C_3H_7)_3P^+C_4H_9I^-$ | 49.0 |

*Yield calculated based on the quantity of prenyl chloride used.

EXAMPLE 9

To 154,3 g of linalool was added 250 ml. of concentrated hydrogen chloride at 5°C. and then 100 ml. of heptane was added and the mixture was separated into two layers and the resultant solution was washed 3 times with 50 ml. of water. To this solution were added 407 g of acetone, 320 g of sodium hydroxide 50% aqueous solution and 6.2 g of tri-n-butyl ethyl phosphonium bromide, and the mixture was heated under reflux for 3 hours.

Three hundred ml. of water was added to the reaction mixture, the organic compound layer was separated from the resultant solution and distilled under reduced pressure to give 75.7 g of geranyl acetone (yield, 39%).

EXAMPLE 10

Into 72.1 g of methyl ethyl ketone, 19.1 g of allyl chloride, 80 g of sodium hydroxide 50% aqueous solution and 1.7 g of stearyl tri-n-butyl phosphonium bromide were introduced into a 500 ml. autoclave and heated with stirring at 65°C. for 4 hours. There was obtained from the reaction mixture 13.4 g of 3-methyl pentene-1-4-one as determined by gas chromatography. The yield was 54.4%.

EXAMPLE 11

Into a round-bottom flask of 200 ml. volume, equipped with a thermometer, a reflux condenser and a stirrer, were introduced 11.9 g of phenyl chloride, 23.2 g of acetone, 32 g of aqueous alkali metal hydroxide solution having 50 weight present concentration, and 0.05 mole of $CH_3(CH_2)_{16}P^+\ (n-C_4H_9)_3Br^-$ as the catalyst and then said mixture was heated at 60°C. for 3 hours under reflux.

The resultant product was treated with the same process disclosed in Example 1.

The yield of 6-methyl-4-heptene-2-one is reached at 53.5 percent.

EXAMPLE 12

Using the same reaction vessel as used in Example 1, 10.45 g of prenyl chloride, 19 g of mesityl oxide, 24 g of 50% aqueous caustic soda solution, and 0.34 g of tetra-n-butyl phosphonium bromide were added to the vessel, and the mixture was allowed to react for 3 hours at 90°C. with stirring.

After completion of the reaction, 10 ml. of water was added to the mixture to dissolve precipitated sodium chloride.

The water layer of said solution was separated from the organic layer, and the organic layer was distilled. The following fractions of distillate were obtained:

| Fraction No. 1 | 62°C./3mmHg | 6.97 g |
|---|---|---|
| Fraction No. 2 | 72.5°C./3mmHg | 5.81 g |

Fraction Nos. 1 and 2 were analyzed using I.R. (infrared ray analysis), NMR (nuclear molecular resonance) and a mass spectrograph and found to contain $\beta$-isopentenyl mesityl oxide and $\alpha$-isopentenyl mesityl oxide, respectively. The yield of said fractions was 42% and 35% respectively.

EXAMPLE 13

Using the same reaction vessel as used in Example 1, 10.45 g of prenyl chloride, 34.8 ml. of acetone, 20.3 g of 65% aqueous caustic soda solution, 5 ml. of n-decane and 0.34 g of tetra-n-bytyl phosphonium bromide were added into the vessel, and the mixture was allowed to react for 8 hours at 30°C. with stirring. After the reaction was complete, 40 ml. of water was added to the resultant solution to dissolve sodium chloride.

The product was methyl heptenone as determined by gas chromatography and the yield was 48% of theoretical.

EXAMPLE 14

Into a round-bottomed flask (300 ml) equipped with a thermometer, a reflux condenser and a stirrer were charged 10.46 g of prenyl chloride, 34.8 ml. of acetone, 18.46 g of 65% NaOH and 0.439 g of (cyclo hexyl)$_3PC_2H_5I$ (1 mole % based on the amount of the prenyl chloride), and the mixture was vigorously stirred for 3 hours under reflux of acetone. After completion of the reaction, the yield of methyl heptenone and the conversion ratio of the prenyl chloride were determined in the usual way to be 51.6% and 94.3% respectively.

EXAMPLE 15

After the repeated reaction employing a catalyst of (cyclohexyl)$_3PC_2H_5I$ described in Example 14 was completed, 30 ml. of H$_2$O was added to dissolve the precipitated sodium chloride. Then the organic layer was separated from the aqueous layer. Upon distilling off the acetone from the organic layer, 10 ml. of ethyl ether was added to produce the precipitate. The obtained precpitate was filtered to leave crystals, which was then washed with ethyl ether. Upon drying under reduced pressure, there was obtained 0.27 g of crystals.

The reaction was conducted for 2 hours by using the thus obtained product as a catalyst under the same conditions as in Example 12. The yield of methylheptenone and the conversion ratio of the prenyl chloride were determined in the usual manner to be 64.5% and 98.5%, respectively.

EXAMPLE 16

To 154.3 g of linalool was added 250 ml. of conc. hydrochloric acid at 5°C and then 100 ml. of heptance. After separation, the organic phase was washed with three portions of 50 ml. of water. To the resulting solution were added 407 g of acetone, 18.64 g of 65% aqueous sodium hydroxide solution and 3.28 g of (cyclo-$C_6H_{11}$)$_3$P.n-$C_4H_9$Br, and the mixture was refluxed with heating for 3 hours. To the reaction mixture was added 300 ml. of water, and the organic layer was separated. Upon distilling off the solvent under reduced pressure, there was obtained 87.3 g of geranyl acetone; yield 45%.

EXAMPLE 17

In an autoclave (500 ml) were placed 72.1 g of methyl ethyl ketone, 19.1 g of allyl chloride, 80 g of 50% aqueous sodium hydroxide solution and 1.07 g of (cyclo-$C_6H_{11}$)$_3$P($CH_2$)$_{11}$·CH Br, and the mixture was reacted at 65°C for 4 hours with stirring. There was obtained 13.1 g of 1-methyl-allylacetone which was quantitatively determined by subjecting the reaction mixture to gas chromatography. Yield, 53%.

To recapitulate, the particular organic halide and particular ketone having the replaceable hydrogen atom in its molecule used in the present invention are not critical. Any organic halide capable of reacting with such a ketone to produce the corresponding substituted ketone is operable in the present invention. Similarly, any ketone having at least one replaceable hydrogen atom on a carbon atom in an alpha position to the carbonyl carbon can be employed in the reaction of the present invention. Broadly therefore, the invention is not to be limited to the exemplary organic halides and ketones provided above. Further, although preferred reaction temperatures and reactant molar ratios have been provided, these ranges may be exceeded by those skilled in the art depending upon the results desired.

While the invention has been described with reference to preferred embodiments thereof, it is to be expressly understood that those skilled in the art can make appropriate changes, modifications and/or substitutions without departing from the spirit and scope thereof. It is the intention therefore that the invention be limited only by the appended claims.

What is claimed is:

1. In a catalytic process for producing substituted ketones by the reaction between organic halides selected from the group consisting of alkyl halides, alkenyl halides, allyl halides, propargyl halides, cycloalkyl halides and benzyl halide and ketones having at least one active hydrogen atom on the carbon atom in the alpha-position to the carbonyl group thereof and selected from the group consisting of alkyl ketones, alkenyl ketones, cycloalkenyl ketones, cycloalkyl ketones and aryl ketones in the presence of an alkali metal hydroxide and a catalyst and optionally water, the improvement comprising conducting said reaction in the presence of a phosphonium salt catalyst having the following formula:

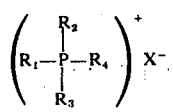  $X^-$ wherein $R_1$, $R_2$, $R_3$ and $R_4$ are independently selected from the group consisting of branched or straight chain alkyl of 1 to 30 carbon atoms, cycloalkyl of 6 to 10 carbon atoms, aryl of 6 to 10 carbon atoms and aralkyl or alkaryl wherein the aryl and alkyl moieties are as defined above and wherein $X^-$ is an inorganic or organic anion capable of dissociating from

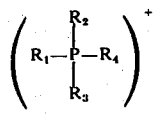

in an aqueous environment, and capable of forming an alkali metal salt with an alkali metal hydroxide.

2. The process in accordance with claim 1, wherein the concentration of said catalyst is in the range of from 0.05 to 20 mole percent based on the molar concentration of said organic halide.

3. The process in accordance with claim 2, wherein the concentration of said catalyst is in the range of from 0.1 to 10 mole percent based on the molar concentration of said organic halide.

4. The process in accordance with claim 1, wherein the molar ratio of said organic halide to said ketone is the range of from 2:1 to 1:20.

5. The process in accordance with claim 1, wherein water is present in the reaction system in an amount in the range of from 2.5 to 10 moles for each mole of said organic halide.

6. The process in accordance with claim 1, wherein the concentration of said alkali metal hydroxide is in the range of from 1.1 to 5 moles per 1 mole of said organic halide, and in the range of from 0.3 to 1 mole for each mole of water present in the reaction system.

7. The process in accordance with claim 1, wherein said alkali metal hydroxide is in the form of a solid.

8. The process in accordance with claim 1, wherein said alkali metal hydroxide is added to the reaction in the form of an aqueous solution.

9. The process in accordance with claim 1, wherein said reaction is conducted at a temperature ranging between 0°C. and 150°C.

10. The process in accordance with claim 1, wherein said anion of said catalyst is selected from the group consisting of chloride, bromide and iodide.

11. The process in accordance with claim 1, wherein said phosphonium salt catalyst is the anionic salt of a compound selected from the group consisting of tetra methyl phosphonium, tetra ethyl phosphonium, methyl tri-propyl phosphonium, diethyl dibutyl phosphonium, tributyl methyl phosphonium, butyl tri-propyl phosphonium, dibenzyl butyl methyl phosphonium, dicyclohexyl dimethyl phosphonium, tetra butyl phosphonium, dibenzyl ethyl methyl phosphonium, dibenzyl diethyl phosphonium, benzyl tri-butyl phosphonium, tribenzyl methyl phosphonium, tri-n-butyl ethyl phosphonium, stearyl tri-butyl phosphonium, hexadecyl-tributyl phosphonium lauryl tributyl phosphonium, tricyclohexyl methyl phosphonium, tricyclohexyl ethyl phosphonium, tricyclohexyl n-butyl phosphonium, tricyclohexyl isobutyl phosphonium, tricyclohexyl n-propyl phosphonium, tricyclohexyl isopropyl phosphonium, tricyclohexyl amyl phosphonium, tricyclohexyl hexyl phosphonium, tricyclohexyl heptyl phosphonium, tricyclohexyl decyl phosphonium, tricyclohexyl lauryl phosphonium, tricyclohexyl tetradecyl phosphonium, tricyclohexyl hexadecyl phosphonium, tricyclohexyl stearyl phosphonium, tetracyclohexyl phosphonium, tricyclohexyl benzyl phosphonium, tri-4-methylcyclohexyl ethyl phosphonium and tri-4-methylcyclohexyl n-butyl phosphonium.

12. The process in accordance with claim 1, wherein said organic halide is an alkyl halide.

13. The process in accordance with claim 1, wherein said organic halide is an alkenyl halide.

14. The process in accordance with claim 13, wherein said organic halide is 1-chloro-3-methyl-2-butene.

15. The process in accordance with claim 1, wherein said organic halide is an allyl halide.

16. The process in accordance with claim 1, wherein said organic halide is a propargyl halide.

17. The process in accordance with claim 1, wherein said organic halide is cyclohexyl halide.

18. The process in accordance with claim 1, wherein said organic halide is benzyl halide.

19. The process in accordance with claim 1, wherein said ketone is an alkyl ketone.

20. The process in accordance with claim 19, wherein said ketone is methyl ethyl ketone.

21. The process in accordance with claim 1, wherein said ketone is an unsaturated ketone.

22. The process in accordance with claim 1, wherein said ketone is an aliphatic cyclic ketone.

23. The process in accordance with claim 1, wherein said ketone is camphor, acetophenone or phenyl acetone.

24. The process in accordance with claim 1, wherein said catalyst comprises a mixture of two or more phosphonium salt compounds.

25. The process in accordance with claim 1, wherein said reaction is continued until substantially all of the organic halide component has been consumed and converted to a substituted ketone.

26. The process in accordance with claim 1, wherein said organic halide is geranyl bromide.

* * * * *